United States Patent [19]
Bombardelli et al.

[11] Patent Number: 5,808,137
[45] Date of Patent: Sep. 15, 1998

[54] CHALCONES AND ESTERS THEREOF WITH ANTIPROLIFERATIVE ACTIVITY IN UTERUS, OVARY AND BREAST TUMORS

[75] Inventors: Ezio Bombardelli, Milan; Salvatore Mancuso; Franco Delle Monache, both of Rome, all of Italy

[73] Assignee: Indena S.p.A., Milan, Italy

[21] Appl. No.: 849,767

[22] PCT Filed: Dec. 4, 1995

[86] PCT No.: PCT/EP95/04770

§ 371 Date: Jun. 12, 1997

§ 102(e) Date: Jun. 12, 1997

[87] PCT Pub. No.: WO96/19209

PCT Pub. Date: Jun. 27, 1996

[30] Foreign Application Priority Data

Dec. 20, 1994 [IT] Italy .................................. MI94A2568

[51] Int. Cl.⁶ ........................... C07C 67/02; C07C 53/00
[52] U.S. Cl. ........................ 560/255; 560/138; 554/229; 554/228; 554/224
[58] Field of Search ............................. 560/138; 554/229, 554/228, 224

[56] References Cited

U.S. PATENT DOCUMENTS 3,928,421 12/1975 Kyogoku et al. .................... 260/479 R
5,106,871 4/1992 Komazawa et al. ..................... 514/571
5,234,951 8/1993 Komazawa et al. ..................... 514/546

FOREIGN PATENT DOCUMENTS

WO 91/17749 11/1991 WIPO .
WO 93/01824 2/1993 WIPO .

OTHER PUBLICATIONS

*IL Farmaco* vol. 30, pp. 326–342, 1975 New Prenylated Chalcones From Lonchocanpus Neuroscapha Benth. de Lima et al.
*IL Farmaco* vol. 30, pp. 449–455, 1975 Synthesis of The Prenylated Chalcones From Corda Piaca. Lupi et al.
*IL Farmaco* vol. 32, pp. 261–269, 1977 Synthetic Analogs of Natural Prenylated and Chromene Chalcones. Lupi et al.
R. De Vincenzo et al., "Effect of synthetic and naturally occurring chalcones on ovarian cancer cell growth: structure–activity relationships", *Anti–Cancer Drug Des.*, vol. 10, No. 4 (1995) pp. 481–490.

*Primary Examiner*—Gary Geist
*Assistant Examiner*—Brian J. Davis
*Attorney, Agent, or Firm*—Pennie & Edmonds LLP

[57] ABSTRACT

The present invention relates to the use of some natural or synthetic chalcones and the esters thereof with straight or branched aliphatic acids, saturated and unsaturated, containing up to 22 carbon atoms in the therapy and prevention of the uterus, ovary and breast tumors, as well as the formulations containing them. Chalcones such as isocordoin, cordoin, 2-hydroxyderricin, 2',4'-dihydroxychalcone, 4,2',4'-trihydroxychalcone have a marked affinity to the estrogen receptors of type II and an antiproliferative activity on uterus, ovary and breast tumor cell lines. These molecules proved to be useful both in therapy and in the prevention of such tumors.

15 Claims, No Drawings

CHALCONES AND ESTERS THEREOF WITH ANTIPROLIFERATIVE ACTIVITY IN UTERUS, OVARY AND BREAST TUMORS

TECHNICAL FIELD

The present invention relates to the use of chalcone compounds or the esters thereof with straight or branched aliphatic acids, saturated and unsaturated containing up to 22 carbon atoms, in the therapy and prevention of uterus, ovary and breast tumours, as well as the formulations containing them.

BACKGROUND ART

Recently, some flavonoids proved to have anticancer activity (Cancer Research 48, 5754, 1988) and chemopreventive activity in some tumours (J. Nat. Prod. 53, 23, 1990). In particular quercetin, a flavonoid almost ubiquitous in plants, has shown some inhibiting activity on the proliferation of human leukemia cells (Br. J. of Haematology 75, 489, 1990) and on other cell lines (Br. J. Cancer 62, 942, 1990—Int. J. Cancer 46, 1112, 1990—Cancer Chemother. Pharmacol. 28, 255, 1991—Gynecologic Oncology 45, 13, 1991, 1992) besides a synergistic activity with the conventional chemotherapeutics. Although the mechanism of such an inhibiting action on proliferation is unknown, it is likely to be related to the interaction of this flavonoid with the estrogen receptors of type II (J. Steroid Biochem. 30, 71, 1988). These sites have first been described by Clark (J. Biol. Chem. 253, 7630, 1978) in 1978 in the rat uterus while displaying the same steroid and tissue specificity are distinct from the "true" estrogen receptors (ER) since they are present in a higher concentration than ER and have a lower apparent affinity dissociation constant (KD: 10–20 nM) for estradiol than ER (KD: 0.2–1 nM).

SUMMARY OF THE INVENTION

Now it has surprisingly been found that the chalcone-structure compounds isocordoin, 4-hydroxyderricin, 2-hydroxyderricin, 3-hydroxyderricin, 2',4'-dihydroxychalcone, 4,2',4'-trihydroxychalcone and cordoin have a remarkable affinity to estrogen receptors of type II, extremely higher than that of the known products, together with a marked antiproliferative activity on uterus, ovary and breast tumour cell lines.

DETAILED DESCRIPTION OF THE PREFERRED EMBODIMENTS

The structures of the compounds cited above are as follows:

|  | $R_1$ | $R_2$ | $R_3$ | $R_4$ | $R_5$ |
|---|---|---|---|---|---|
| S1 Isocordoin | H | H | Prenyl | H | H |
| S2 4-hydroxyderricin | Me | OH | Prenyl | H | H |
| S3 2-hydroxyderricin | Me | H | Prenyl | OH | H |
| S4 3-hydroxyderricin | Me | H | Prenyl | H | OH |
| S5 2',4'-dihydroxychalcone | H | H | H | H | H |
| S6 4,2',4'-trihydroxychalcone | H | OH | H | H | H |
| S7 Cordoin | Prenyl | H | H | H | H |

Other chalcones strictly related to the former as far as the chemical structure is concerned, such as 4-hydroxycordoin and dihydrocordoin, whose structures are reported below, show no affinity to the above mentioned receptors.

| Chalcones | $R_1$ | $R_2$ | $R_3$ |
|---|---|---|---|
| S8 4-hydroxycordoin | prenyl | OH | H |
| S9 Dihydrocordoin | prenyl | H | H |

Therefore the invention, in a first aspect, provides the use of the compounds of formula (I) for the preparation of medicaments with anticancer activity, in particular for the treatment of tumours expressing estrogen receptors of type II.

The invention, according to a further aspect, also provides the esters of the compounds of formula (I) with straight or branched aliphatic acids, saturated or unsaturated, containing up to 22 carbon atoms. Particularly preferred are the esters with acetic, butyric, palmitic or ximeninic acids.

The esters of the invention can be administered by the oral route and they are likely to behave as pro-drugs for chalcones I.

Finally, the invention provides pharmaceutical compositions containing compounds I or the esters thereof as active ingredients, in admixture with suitable excipients.

Compounds (I) can be prepared according to conventional methods reported by II Farmaco, 30, 449–55, 1975; II Farmaco, 32, 261–69, 1977; Il Farmaco, 30, 326–42, 1975.

The affinity of compounds I to the estrogen receptors of type II and the antiproliferative activity on ovary tumour cells is reported in the following table.

TABLE

Binding affinity to estrogen receptors of type II and
antiproliferative activity on OVCA 433 cancer cells in vitro.

| Chalcones | $IC_{50}$** (uM) | $IC_{50}$*** (uM) |
|---|---|---|
| S1 | 1.2 | 1.2 |
| S2 | 17.0 | 10.6 |
| S3 | 4.2 | 18.0 |
| S4 | 5.0 | 12.1 |
| S5 | 2.5 | 0.6 |
| S6 | 5.0 | 3.2 |
| S7 | 6.0 | 4.2 |

**Concentration giving a 50% inhibition on cell proliferation.
***Concentration giving a 50% dispiacement* of labelled estradiol (40 nM) from the receptor.

The evaluation of the estrogen receptor binding has been carried out on tumour cells of ovary and other organs. Cells were growth in a monolayer culture on the minimum essential medium added with calf serum and with 200 units/ml of penicillin to maintain the medium sterile. In order to make the tests reproducible, the cells were trypsinated every week and placed on plates at a density of $8 \times 10^{-4}$ and incubated at 37° C. under air atmosphere containing 5% $CO_2$ and humidity. To evaluate the activity of the compounds, the cells were placed into wells (Falcon 3046, Becton Dickinson NY) at a concentration of $1 \times 10^{-5}$/ml in the minimum amount of substrate. After 24 hours the substrate was replaced with fresh substrate and the chalcones dissolved in absolute ethanol were added. Controls were treated analogously with the carrier, in the absence of the active ingredient to test. The treatment described above was repeated at 24 hours time intervals during the 72 hours time of the test. The cells after 24 hours were incubated with scalar amounts of labelled estradiol ($^3$H-E2 40Ci/mmol Amershan UK) alone or in the presence of a 100-fold amount of diethylstilbestrol at 4° C. for 2.5 hours. At the end of the incubation time, the cells were quickly washed with fresh substrate and incubated for 30 minutes with 1M NaOH. The radioactivity was measured by means of a scintiller and the binding specificity was calculated as the difference between the preparations containing or not diethylstilbestrol. The results are expressed as the number of binding sites per cell, according to conventional methods. The inhibition on the cell proliferation is evaluated by direct count of the cells comparing the growth of the controls versus that of the treated.

The compounds of the invention inhibited in vivo the cell proliferation, as proved by measurement of the size of the tumours implanted into the nude athymic mouse, according to the conventional conditions of literature. The treatment of the animals with doses ranging from 1 to 100 mg/kg evidenced the marked regression of the studied tumours until their disappearance in a high percentage of individuals. In the man, compounds I showed activity on ovary, breast and uterus tumours higher than that of known medicaments such as Tamoxifen.

In the above cited tests, the esters of isocordoin, cordoin and 2',4'-dihydroxychalcone showed a particularly marked activity.

The compounds of the invention can be advantageously administered orally or by infusion; for the oral administration, natural or synthetic phospholipids turned out to be particularly useful since they form stable liposoluble complexes with chalcones; medium chain triglycerides and the related excipients also proved to be useful. The dosages of the compounds of the invention can vary within wide ranges, for example from 10 to 300 mg/day, mainly administered by the oral route.

EXAMPLES

The following examples further illustrate the invention.

Example I—Preparation of Cordoin Ximeninate 7 g of 4-O-prenyl-2-hydroxyacetophenone are reacted with 7 g of benzaldehyde in 10 g of piperidine and 70 ml of ethanol at 60°–70° C. After 36 hours the solvent is removed under vacuum and the residue is taken up with 100 ml of benzene which is washed thoroughly with 2N HCl. After removing benzene the residue is purified on a silica gel column to obtain 3.5 g of cordoin. The resulting cordoin is reacted in 20 ml of anhydrous pyridine with 3 g of ximeninic acid chloride. The reaction mixture is poured into water and the product is extracted with methylene chloride. After crystallization from methanol, 4.2 g of cordoin ximeninate are obtained, having m.p. 164°–166° C.

Example II—Preparation of Isocordoin Palmitate 10 g of 3-C-prenylresacetophenone and 10 g of p-hydroxybenzaldehyde are dissolved in 15 g of piperidine and 200 ml of absolute ethanol and maintained for 4 hours at 60° C. After removing the solvent, the residue is suspended in 50 ml of 2N HCl and the product is extracted with methylene chloride. After removing the chlorinated solvent, the residue is purified on silica gel to obtain 4.1 g of isocordoin having m.p. 160°–1° C. This product is reacted with 8 g of palmitoyl chloride in 30 ml of anhydrous pyridine. After dilution of the reaction mixture with water and purification on silica gel, 6.2 g of dipalmitoylisocordoin are obtained, having m.p. 131°–132° C.

Example III—Preparation of Cordoin and Isocordoin Acetates and Butyrates.

These products are prepared according to the examples I and II using respectively the chlorides or the anhydrides of the corresponding acids. (Cordoin acetate m.p. 131°–3° C.; cordoin butyrate m.p. 124°–6° C.).

Example IV—Preparation of the Complex of Isocordoin with Dipalmitoyl Phosphatidylcholine 3.08 g of isocordoin are suspended in 30 ml of methylene chloride and added with 7.9 g of dipalmitoyl phosphatidylcholine and left to react for 1 hour with stirring. When the reagents are completely dissolved, the reaction mixture is concentrated to small volume and the concentrate is poured into in 50 ml of n-hexane. The precipitated solid material is filtered and dried at 40° C. overnight under vacuum, to obtain 7.2 g of phospholipid isocordoin complex having m.p. 70° C.

What is claimed is:

1. An ester of isocordoin, cordoin, 4-hydroxyderricin, 2-hydroxyderricin, 3-hydroxyderricin, 2',4'-dihydroxychalcone or 4,2',4'-trihydroxychalcone with palmitic or ximeninic acid.

2. The cordoin or isocordoin esters according to claim 1.

3. A complex of one of the esters of claim 1 with a phospholipid.

4. A pharmaceutical composition comprising an active ingredient of an ester according to claim 1 in admixture with an excipient.

5. A pharmaceutical composition comprising an active ingredient of an ester according to claim 2 in admixture with an excipient.

6. A pharmaceutical composition comprising an active ingredient of the complex according to claim 3 in admixture with an excipient.

7. The pharmaceutical composition of claim 4, wherein the active ingredient is present in an amount from 10 mg/day to 300 mg/day.

8. A compound comprising an ester of isocordoin, cordoin, 4-hydroxyderricin, 2-hydroxyderricin, or 3-hydroxyderricin with a straight or branched $C_{1-22}$ aliphatic acid.

9. The compound of claim 8, wherein the acid is acetic, butyric, palmitic or ximeninic acid.

10. A complex of one of the esters of claim 8 with a phospholipid.

11. A pharmaceutical composition comprising an active ingredient of an ester according to claim 8 in admixture with an excipient.

12. A pharmaceutical composition comprising an active ingredient of the complex of claim 11 in admixture with an excipient.

13. The pharmaceutical composition of claim 11, wherein the active ingredient is present in an amount from 10 mg/day to 300 mg/day.

14. A complex of a phospholipid with a chalcone comprising isocordoin, cordoin, 4-hydroxyderricin, 2-hydroxyderricin, 3-hydroxyderricin, 2',4'-dihydroxychalcone, or 4,2', 4'-trihydroxychalcone.

15. The complex of claim 14, wherein the chalcone is selected from the group consisting of isocordoin, cordoin, 2',4'-dihydroxychalcone, and mixtures thereof.

* * * * *